United States Patent
Zang et al.

(10) Patent No.: US 12,263,203 B2
(45) Date of Patent: Apr. 1, 2025

(54) BTNL9 AND ERMAP AS NOVEL INHIBITORS OF THE IMMUNE SYSTEM FOR IMMUNOTHERAPIES

(71) Applicant: Albert Einstein College of Medicine, Bronx, NY (US)

(72) Inventors: Xingxing Zang, New York, NY (US); Kaya Ghosh, Bronx, NY (US)

(73) Assignee: Albert Einstein College of Medicine, Bronx, NY (US)

(*) Notice: Subject to any disclaimer, the term of this patent is extended or adjusted under 35 U.S.C. 154(b) by 286 days.

(21) Appl. No.: 16/867,500

(22) Filed: May 5, 2020

(65) Prior Publication Data
US 2020/0338161 A1    Oct. 29, 2020

Related U.S. Application Data

(63) Continuation of application No. 15/525,092, filed as application No. PCT/US2015/060292 on Nov. 12, 2015, now abandoned.

(60) Provisional application No. 62/084,124, filed on Nov. 25, 2014.

(51) Int. Cl.
| | | |
|---|---|---|
| A61K 39/395 | (2006.01) | |
| A61K 38/17 | (2006.01) | |
| A61P 35/00 | (2006.01) | |
| C07K 16/18 | (2006.01) | |
| C07K 16/30 | (2006.01) | |
| C07K 16/32 | (2006.01) | |
| C07K 14/47 | (2006.01) | |

(52) U.S. Cl.
CPC ........ *A61K 38/1709* (2013.01); *A61K 39/395* (2013.01); *A61K 39/39558* (2013.01); *A61P 35/00* (2018.01); *C07K 16/18* (2013.01); *C07K 16/30* (2013.01); *C07K 16/32* (2013.01); *C07K 14/47* (2013.01); *C07K 2319/30* (2013.01)

(58) Field of Classification Search
None
See application file for complete search history.

(56) References Cited

U.S. PATENT DOCUMENTS

2013/0101590 A1* 4/2013 Arnett .............. C07K 14/70503
424/139.1

FOREIGN PATENT DOCUMENTS

WO   WO2008154516   * 12/2008
WO   2011/127418 A1   10/2011

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
PCT International Search Report and Written Opinion, dated Apr. 19, 2016 in connection with PCT International Application No. PCT/US2015/60292, 13 pages.
Summons to Attend Oral Proceedings, EP Application No. 15863547.4, dated Sep. 29, 2020, 5 pages.

* cited by examiner

*Primary Examiner* — Meera Natarajan
(74) *Attorney, Agent, or Firm* — Perkins Coie LLP

(57) ABSTRACT

Provided are methods of treating a tumor in a subject with a BTNL9-binding antibody. Also provided are methods of treating a tumor in a subject with an ERMAP-binding antibody. A fusion protein comprising a BTNL9 or ERMAP and related compositions and encoding nucleic acids are also provided.

15 Claims, 7 Drawing Sheets
Specification includes a Sequence Listing.

US 12,263,203 B2

BTNL9 AND ERMAP AS NOVEL INHIBITORS OF THE IMMUNE SYSTEM FOR IMMUNOTHERAPIES

CROSS-REFERENCE TO RELATED APPLICATIONS

This application is a continuation of U.S. application Ser. No. 15/525,092, filed May 8, 2017, which is a U.S. national stage entry under 35 U.S.C. § 371 of PCT International Patent Application No. PCT/US2015/060292, filed Nov. 12, 2015, which claims benefit of U.S. Provisional Application No. 62/084,124, filed Nov. 25, 2014, the contents of each of which are incorporated herein by reference into the subject application.

STATEMENT OF GOVERNMENT SUPPORT

This invention was made with government support under grant numbers DK083076 and DK007218 awarded by the National Institutes of Health. The government has certain rights in the invention.

BACKGROUND OF THE INVENTION

The disclosures of all publications, patents, patent application publications and books referred to herein, are hereby incorporated by reference in their entirety into the subject application to more fully describe the art to which the subject invention pertains.

Cancers, autoimmune diseases, infectious diseases, and transplantation rejection are serious public health problems in the US and other countries. The immune system, particularly T cells, plays critical roles in these diseases.

The B7 ligand family and CD28 receptor family control T cell activation and function. Both CTLA-4 and PD-1 are members of the CD28 family, and an antibody against CTLA-4 (Yervoy from Bristol-Myers Squibb) and an antibody against PD-1 (Keytruda, Merck) were approved by the FDA as new drugs for melanoma in 2011 and 2014, respectively. PD-L1 is a member of the B7 family, and antibodies to PD-L1 are in clinical trials with cancer patients. In additional, CTLA-4-Ig (Orencia) was approved by the FDA as a new drug for adult rheumatoid arthritis.

The existing technologies work by blockade of the B7/CD28 family members. The butyrophilin family is related to the B7 family, but their expression and functions in the immune system are largely unknown.

The present invention provides addresses the need for improved therapies and therapeutics based on targeting BTNL9 or ERMAP.

SUMMARY OF THE INVENTION

A method of treating a tumor in a subject comprising administering to the subject an amount of a BTNL9-binding antibody, or BTNL9-binding fragment thereof, sufficient to inhibit a BTNL9 and treat the tumor.

A method of treating a tumor in a subject comprising administering to the subject an amount of a ERMAP-binding antibody, or ERMAP-binding fragment thereof, sufficient to inhibit a ERMAP and treat the tumor.

A method of treating a tumor in a subject comprising administering to the subject an amount of a BTNL2-binding antibody, or BTNL2-binding fragment thereof, sufficient to inhibit a BTNL2 and treat the tumor.

A method of treating an autoimmune disease in a subject comprising administering to the subject an amount of an isolated, plasma-soluble BTNL9 to treat the autoimmune disease.

A method of treating an autoimmune disease in a subject comprising administering to the subject an amount of an isolated, plasma-soluble ERMAP to treat the autoimmune disease.

A method of treating an autoimmune disease in a subject comprising administering to the subject an amount of an isolated, plasma-soluble BTNL2 to treat the autoimmune disease.

An isolated, recombinant fusion polypeptide comprising a BTNL9 fused to an immunoglobulin polypeptide.

An isolated, recombinant fusion polypeptide comprising an ERMAP fused to an immunoglobulin polypeptide.

An isolated, recombinant fusion polypeptide comprising a BTNL2 fused to an immunoglobulin polypeptide.

An isolated chimeric nucleic acid encoding an isolated recombinant fusion polypeptide as described herein.

A composition comprising an isolated recombinant fusion polypeptide as described herein and a carrier.

DETAILED DESCRIPTION OF THE INVENTION

Figure 1A:
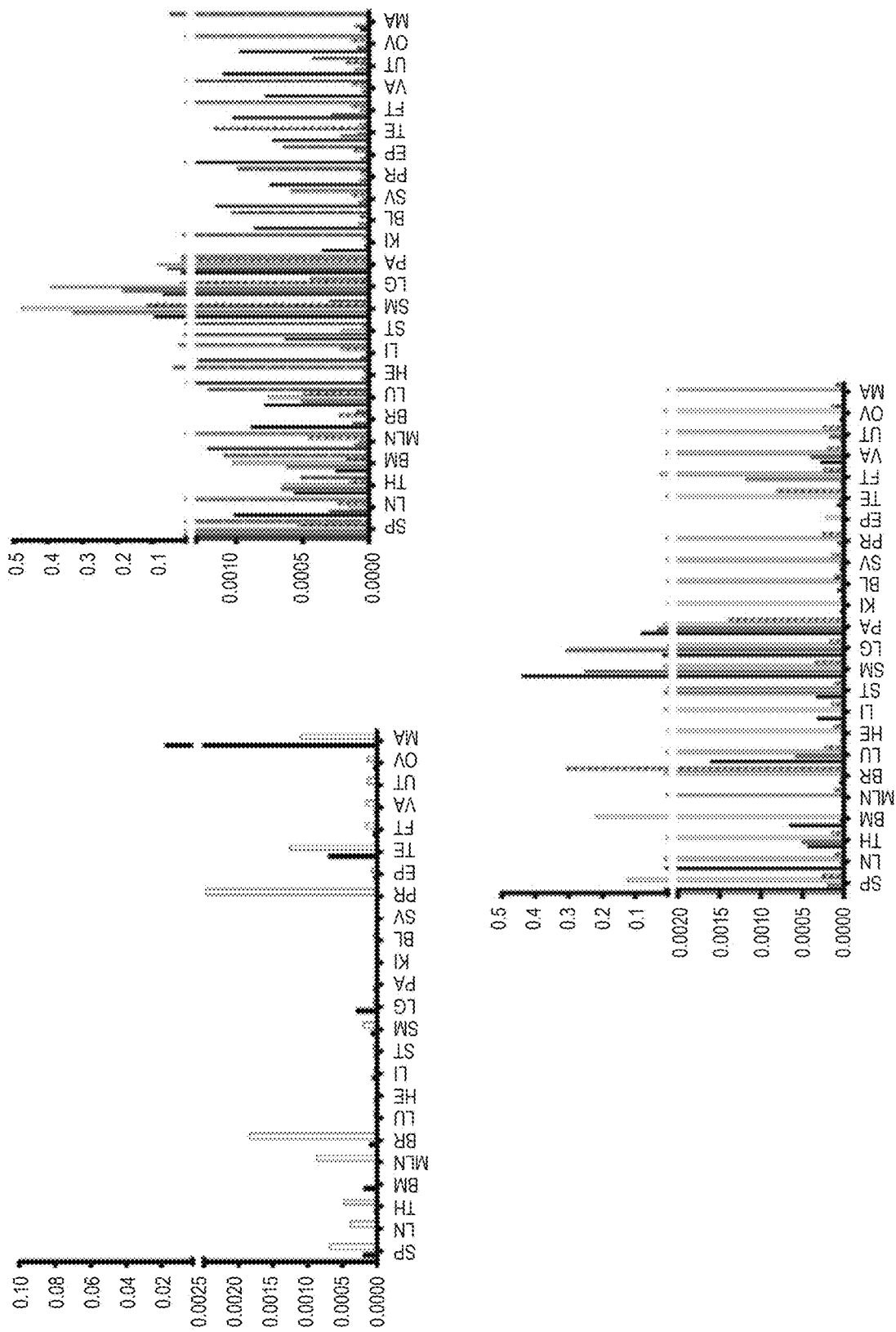
FIG. 1A-1B. mRNA transcripts of BTN and BTNL family members in mouse tissues and antigen-presenting cells relative to the reference gene OAZ1. (A) Transcripts in naïve mouse tissues. Transcripts of BTN family members (upper panel) show that BTN transcripts are most abundant in mammary tissue. Transcripts of BTNL family members with intracellular SPRY domains (center panel) and of those without intracellular SPRY domains (bottom panel) are highest in the small and large intestines. Transcripts are also generally detectable in other tissues, particularly the primary lymphoid organs; MOG transcripts are highest in brain tissue. SP, spleen; LN, pooled inguinal and brachial lymph nodes; TH, thymus; BM, bone marrow; MLN, mesenteric lymph node; BR, brain; LU, lung; HE, heart; LI, liver; ST, stomach; SM, small intestine; LG, large intestine; PA, pancreas; KI, kidney; BL, bladder; SV, seminal vesicles; PR, prostate; EP, epididymis; TE, testis; FT, Fallopian tube; VA, vagina; UT, uterus; OV, ovary; MA, mammary gland. (B) Transcripts in resting and activated antigen-presenting cells (APCs). Transcripts for most genes are detectable in all three professional APCs, are in most cases lower in macrophages compared to dendritic cells and B cells, and are generally not strongly up- or down-regulated upon activation by LPS or PMA+ionomycin.

This invention provides the first disclosure that butyrophilin-like 9 (BTNL9) and erythroblast membrane-associated protein (ERMAP), two members of the butyrophilin family, inhibit T cell functions. A short form of BTNL2 was also strongly inhibitory. In particular, evidence that recombinant proteins of BTNL9 and ERMAP inhibit cell proliferation and cytokine production of T cells and that activated T cells have receptors for BTNL9 and ERMAP is provided. Since BTNL9 and ERMAP are expressed by immune cells or other cells. Applications of targeting these two molecules to enhance immunity (e.g. cancer immunotherapy) or decrease immunity (e.g. therapy of autoimmune diseases) are encompassed. Also, applications of using BTNL2, especially the short or "partial" form are encompassed.

BTNL9 is an inhibitor of the immune system. Therefore blockade of BTNL9-mediated immune suppression with blockers (e.g. monoclonal antibodies to BTNL9) can be used for treatment of human cancers and infectious diseases, while enhancement of BTNL9-mediated immune suppression with soluble proteins (e.g. BTNL9-Ig) can be used for treatment of autoimmune diseases and transplantation.

ERMAP is an inhibitor of the immune system. Therefore blockade of ERMAP-mediated immune suppression with blockers (e.g. monoclonal antibodies to ERMAP) can be used for treatment of human cancers and infectious diseases, and enhancement of ERMAP-mediated immune suppression with soluble proteins (e.g. ERMAP-Ig) can be used for treatment of autoimmune diseases and transplantation.

A method of treating a tumor is provided in a subject comprising administering to the subject an amount of a BTNL9-binding antibody, or BTNL9-binding fragment thereof, sufficient to inhibit a BTNL9 and treat the tumor.

Also provided is a method of treating a tumor in a subject comprising administering to the subject an amount of a ERMAP-binding antibody, or ERMAP-binding fragment thereof, sufficient to inhibit a ERMAP and treat the tumor.

Also provided is a method of treating a tumor in a subject comprising administering to the subject an amount of a BTNL2-binding antibody, or BTNL2-binding fragment thereof, sufficient to inhibit a BTNL2 and treat the tumor.

In an embodiment, the BTNL9 is a human BTNL9. In an embodiment, the ERMAP is a human ERMAP. In an embodiment, the BTNL2 is a human BTNL2.

In an embodiment of the methods, the tumor is a tumor of a breast, lung, thyroid, melanoma, pancreas, ovary, liver, bladder, colon, prostate, kidney, esophagus, or is a hematological tumor, or wherein the tumor is a lymphoid organ tumor.

In an embodiment of the methods, the antibody is administered as an adjunct to an additional anti-cancer therapy for the tumor.

In an embodiment of the methods, the amount of a BTNL9-binding antibody is administered. In an embodiment of the methods, the BTNL9-binding antibody binds an IgV1 domain of human BTNL9.

In an embodiment of the methods, the amount of a ERMAP-binding antibody is administered.

In an embodiment of the methods, the amount of a BTNL2-binding antibody is administered. In an embodiment of the methods, the BTNL2-binding antibody binds an IgV1 domain of human BTNL2.

In an embodiment of the methods, the fragment of the antibody is administered.

In an embodiment of the methods, the antibody is a monoclonal antibody.

In an embodiment of the invention, the BTNL9 is human BTNL9. In an embodiment human BTNL9 protein has the sequence:

(SEQ ID NO: 1)
MVDLSVSPDSLKPVSLTSSLVFLMHLLLLQPGEPSSEVKVLGPEYPILAL

VGEEVEFPCHLWPQLDAQQMEIRWFRSQTFNVVHLYQEQQELPGRQMPAF

RNRTKLVKDDIAYGSVVLQLHSIIPSDKGTYGCRFHSDNFSGEALWELEV

AGLGSDPHLSLEGFKEGGIQLRLRSSGWYPKPKVQWRDHQGQCLPPEFEA

IVWDAQDLFSLETSVVVRAGALSNVSVSIQNLLLSQKKELVVQIADVFVP

GASAWKSAFVATLPLLLVLAALALGVLRKQRRSREKLRKQAEKRQEKLTA

ELEKLQTELDWRRAEGQAEWRAAQKYAVDVTLDPASAHPSLEVSEDGKSV

SSRGAPPGPAPGHPQRFSEQTCALSLERFSAGRHYWEVHVGRRSRWFLGA

CLAAVPRAGPARLSPAAGYWVLGLWNGCEYFVLAPHRVALTLRVPPRRLG

VFLDYEAGELSFFNVSDGSHIFTFHDTFSGALCAYFRPRAHDGGEHPDPL

TICPLPVRGTGVPEENDSDTWLQPYEPADPALDWW.

In an embodiment of the invention, the ERMAP is human ERMAP. In an embodiment human ERMAP protein has the sequence:

(SEQ ID NO: 2)
MEMASSAGSWLSGCLIPLVFLRLSVHVSGHAGDAGKFHVALLGGTAELLC

PLSLWPGTVPKEVRWLRSPFPQRSQAVHIFRDGKDQDEDLMPEYKGRTVL

VRDAQEGSVTLQILDVRLEDQGSYRCLIQVGNLSKEDTVILQVAAPSVGS

LSPSAVALAVILPVLVLLIMVCLCLIWKQRRAKEKLLYEHVTEVDNLLSD

-continued

```
HAKEKGKLHKAVKKLRSELKLKRAAANSGWRRARLHFVAVTLDPDTAHPK

LILSEDQRCVRLGDRRQPVPDNPQRFDFVVSILGSEYFTTGCHYWEVYVG

DKTKWILGVCSESVSRKGKVTASPANGHWLLRQSRGNEYEALTSPQTSFR

LKEPPRCVGIFLDYEAGVISFYNVTNKSHIFTFTHNFSGPLRPFFEPCLH

DGGKNTAPLVICSELHKSEESIVPRPEGKGHANGDVSLKVNSSLLPPKAP

ELKDIILSLPPDLGPALQELKAPSF.
```

In an embodiment of the invention, the BTNL2 is human BTNL2. In an embodiment human BTNL2 protein has the sequence:

```
                                         (SEQ ID NO: 3)
MVDCPRYSLSGVAASFLFVLLTIKHPDDFRVVGPNLPILAKVGEDALLTC

QLLPKRTTAHMEVRWYRSDPAMPVIMYRDGAVVTGLPMEGYGGRAEWMED

STEEGSVALKIRQVQPSDDGQYWCRFQEGDYWRETSVLLQVAALGSSPNI

HVEGLGEGEVQLVCTSRGWFPEPEVHWEGIWGEKLMSFSENHVPGEDGLF

YVEDTLMVRNDSVETISCFIYSHGLRETQEATIALSERLQTELVSVSVIG

HSQPSPVQVGENIELTCHLSPQTDAQNLEVRWLRSRYYPAVHVYANGTHV

AGEQMVEYKGRTSLVTDAIHEGKLTLQIHNARTSDEGQYRCLFGKDGVYQ

EARVDVQVTAVGSTPRITREVLKDGGMQLRCTSDGWFPRPHVQWRDRDGK

TMPSFSEAFQQGSQELFQVETLLLVTNGSMVNVTCSISLPLGQEKTARFP

LSDSKI.
```

In an embodiment of the invention, the short form of BTNL2 is a short form of human BTNL2. In an embodiment the short form of human BTNL2 has the sequence:

```
                                         (SEQ ID NO: 4)
MVDCPRYSLSGVAASFLFVLLTIKHPDDFRVVGPNLPILAKVGEDALLTC

QLLPKRTTAHMEVRWYRSDPAMPVIMYRDGAVVTGLPMEGYGGRAEWMED

STEEGSVALKIRQVQPSDDGQYWCRFQEGDYWRETSVLLQVAALGSSPNI

HVEGLGEGEVQLVCTSRGWFPEPEVHWEGIWGEKLMSFSENHVPGEDGLF

YVEDTLMVRNDSVETISCFIYSHGLRETQEATIALSERLQTELVSVSVIG

HSQPSPVQVG.
```

Protein sequence of the IgV1 domain of human BTNL2:

```
                                         (SEQ ID NO: 5)
KQSEDFRVIGPAHPILAGVGEDALLTCQLLPKRTTMHVEVRWYRSEPSTP

VFVHRDGVEVTEMQMEEYRGWVEWIENGIAKGNVALKIHNIQPSDNGQYW

CHFQDGNYCGETSLLLKVAGLGSAPSIHM.
```

Protein sequence of the IgV1 domain of human BTNL9:

```
                                         (SEQ ID NO: 6)
EVKVLGPEYPILALVGEEVEFPCHLWPQLDAQQMEIRWFRSQTFNVVHLY

QEQQELPGRQMPAFRNRTKLVKDDIAYGSVVLQLHSIIPSDKGTYGCRFH

SDNFSGEALWELEVAGLGSDPHLS.
```

In an embodiment of the methods, the tumor is a tumor of a breast, lung, thyroid, melanoma, pancreas, ovary, liver, bladder, colon, prostate, kidney, esophagus, or is a hematological tumor. In an embodiment of the methods, the tumor is a hematological tumor and is a leukemia or a lymphoma. In an embodiment of the methods, the tumor is a tumor of the breast and is a triple negative breast cancer. In an embodiment of the methods, the tumor is a tumor of a lymphoid organ.

Also provided is an isolated fusion protein comprising a soluble portion of an BTNL9 and an Fc portion of an immunoglobulin G.

Also provided is an isolated fusion protein comprising a soluble portion of an ERMAP and an Fc portion of an immunoglobulin G.

An isolated chimeric nucleic acid encoding an isolated fusion protein as described herein is provided.

A composition comprising the isolated fusion protein as described herein and a carrier is provided.

In an embodiment, the composition is a pharmaceutical composition, and the carrier is a pharmaceutical carrier.

Also provided is a method of treating an autoimmune disease in a subject comprising administering to the subject an amount of an isolated, plasma-soluble BTNL9 to treat the autoimmune disease.

Also provided is a method of treating an autoimmune disease in a subject comprising administering to the subject an amount of an isolated, plasma-soluble ERMAP to treat the autoimmune disease.

Also provided is a method of treating an autoimmune disease in a subject comprising administering to the subject an amount of an isolated, plasma-soluble BTNL2 to treat the autoimmune disease.

In an embodiment, the BTNL-2 comprises SEQ ID NO:4 but does not comprise SEQ ID NO:3.

In an embodiment, the plasma-soluble BTNL9, or the plasma-soluble ERMAP, respectively, comprises an BTNL9 fused to an immunoglobulin polypeptide, or an ERMAP fused to an immunoglobulin polypeptide, respectively.

In an embodiment, the plasma-soluble BTNL2 comprises an BTNL2 fused to an immunoglobulin polypeptide.

In an embodiment, the immunoglobulin polypeptide comprises an Fc portion of an immunoglobulin G.

Also provided is an isolated, recombinant fusion polypeptide comprising a BTNL9 fused to an immunoglobulin polypeptide. Also provided is an isolated, recombinant fusion polypeptide comprising an IgV1 domain of human BTNL9 fused to an immunoglobulin polypeptide. In an embodiment, the IgV1 domain of human BTNL9 comprises SEQ ID NO:6.

Also provided is an isolated, recombinant fusion polypeptide comprising an ERMAP fused to an immunoglobulin polypeptide.

Also provided is an isolated, recombinant fusion polypeptide comprising a BTNL2 fused to an immunoglobulin polypeptide. In an embodiment, the BTNL-2 comprises SEQ ID NO:4 but does not comprise SEQ ID NO:3. Also provided is an isolated, recombinant fusion polypeptide comprising an IgV1 domain of human BTNL2 fused to an immunoglobulin polypeptide. In an embodiment, the IgV1 domain of human BTNL2 comprises SEQ ID NO:5.

Also provided is an isolated chimeric nucleic acid encoding an isolated recombinant fusion polypeptide as described herein.

Also provided is a composition comprising the isolated recombinant fusion polypeptide as described herein and a carrier. In an embodiment, the compositions is a pharmaceutical composition, and comprises a pharmaceutical carrier.

The term "ERMAP-Ig" fusion protein as used herein means a fusion protein constructed of a portion of an immunoglobulin and an active portion of a ERMAP, or proteins having an identical sequence thereto. In a preferred embodiment, the active portion of a ERMAP is a soluble portion of ERMAP. In an embodiment, the ERMAP has the sequence of a human ERMAP. In an embodiment, the portion of an immunoglobulin is a portion of an IgG or an IgM. In an embodiment, it as a portion of an IgG. The IgG portion of the fusion protein can be, e.g., any of an IgG1, IgG2, IgG2a, IgG2b, IgG3 or IgG4 or a portion thereof. In an embodiment, the portion is an Fc region. In an embodiment the fusion protein comprises a sequence identical to an Fc portion of a human IgG1, human IgG2, human IgG2a, human IgG2b, human IgG3 or human IgG4. In an embodiment the fusion protein comprises a sequence identical to an Fc portion of a human IgG1. The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, by recombinantly engineering the nucleic acid encoding the fusion protein.

The term "BTNL9-Ig" fusion protein as used herein means a fusion protein constructed of a portion of an immunoglobulin and an active portion of a BTNL9, or proteins having an identical sequence thereto. In an embodiment, the active portion of a BTNL9 is a soluble portion of BTNL9. In an embodiment, the BTNL9 has the sequence of a human BTNL9.

The term "BTNL2-Ig" fusion protein as used herein means a fusion protein constructed of a portion of an immunoglobulin and an active portion of a BTNL2, or proteins having an identical sequence thereto. In an embodiment, the active portion of a BTNL2 is a soluble portion of BTNL2. In an embodiment, the BTNL2 has the sequence of a human BTNL2. In an embodiment, the BTNL-2 comprises SEQ ID NO:4 but does not comprise SEQ ID NO:3.

In an embodiment, the portion of an immunoglobulin of the fusion proteins is a portion of an IgG or an IgM. In an embodiment, it as a portion of an IgG. The IgG portion of the fusion protein can be, e.g., any of an IgG1, IgG2, IgG2a, IgG2b, IgG3 or IgG4 or a portion thereof. In an embodiment, the portion is an Fc region. In an embodiment the fusion protein comprises a sequence identical to an Fc portion of a human IgG1, human IgG2, human IgG2a, human IgG2b, human IgG3 or human IgG4. In an embodiment the fusion protein comprises a sequence identical to an Fc portion of a human IgG1. The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, by recombinantly engineering the nucleic acid encoding the fusion protein.

In an embodiment, the Fc portion of the Ig is used in the fusion proteins as described herein. The presence of the Fc domain markedly increases the plasma half-life of the attached protein, which prolongs therapeutic activity. In addition, the Fc domain also enables the fusion protein to interact with Fc-receptors. In an embodiment, the ERMAP-Ig comprises a ERMAP portion linked to an Fc domain. In an embodiment, the ERMAP portion is bound directly by a peptide bond to the Fc domain. In an embodiment, the ERMAP portion is linked to the Fc domain through a linker. In an embodiment, the BTNL9-Ig comprises a BTNL9portion linked to an Fc domain. In an embodiment, the BTNL9 portion is bound directly by a peptide bond to the Fc domain. In an embodiment, the BTNL9 portion is linked to the Fc domain through a linker.

In an embodiment, the fusion protein (or fusion polypeptide) is linked via a peptide linker which permits flexibility. In an embodiment, the linker is rigid. In an embodiment the linker is cleavable. Non-limiting examples of flexible linkers within the scope of the invention are $G_n$, and GGGGS, and $(GGGGS)_n$ where n=2, 3, 4 or 5 (SEQ ID NO:7). Non-limiting examples of rigid linkers within the scope of the invention are $(EAAAK)_n$ (SEQ ID NO:8), $(XP)_n$. Non-limiting examples of cleavable linkers within the scope of the invention include disulfide links and protease cleavable linkers. In a preferred embodiment, the linker is a peptide linker.

In an embodiment, the Fc domain has the same sequence or 95% or greater sequence similarity with a human IgG1 Fc domain. In an embodiment, the Fc domain has the same sequence or 95% or greater sequence similarity with a human IgG2 Fc domain. In an embodiment, the Fc domain has the same sequence or 95% or greater sequence similarity with a human IgG3 Fc domain. In an embodiment, the Fc domain has the same sequence or 95% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua et al, 2006; Yeung et al, 2009).

In an embodiment, the fusion protein described herein is recombinantly produced. In an embodiment, the fusion protein is produced in a eukaryotic expression system. In an embodiment, the fusion protein produced in the eukaryotic expression system comprises glycosylation at a residue on the Fc portion corresponding to Asn297.

In an embodiment, the fusion protein is a homodimer. In an embodiment, the fusion protein is monomeric. In an embodiment, the fusion protein is polymeric.

In an embodiment, a BTNL9-Ig is prepared by fusing the coding region of the extracellular domain of a BTNL9 having the same sequence as a human extracellular domain of a BTNL9 to a polypeptide having the same sequence as a human IgG1 Fc. Such can be made in any way known in the art, including by transfecting an appropriate cell type with a recombinant nucleic acid encoding the fusion protein. The BTNL2-Ig fusion protein can be made in an analogous matter, as can the other fusion proteins mentioned herein.

In an embodiment, a ERMAP-Ig is prepared by fusing the coding region of the extracellular domain of a ERMAP having the same sequence as a human extracellular domain of a ERMAP to a polypeptide having the same sequence as a human IgG1 Fc. Such can be made in any way known in the art, including by transfecting an appropriate cell type with a recombinant nucleic acid encoding the fusion protein.

In an embodiment, of all aspects of the invention described herein reciting a subject, the subject is a human Cancers, including tumors, treatable by the invention include of the nasopharynx, pharynx, lung, bone, brain, sialaden, stomach, esophagus, testes, ovary, uterus, endometrium, liver, small intestine, appendix, colon, rectum, gall bladder, pancreas, kidney, urinary bladder, breast, cervix, vagina, vulva, prostate, thyroid, skin, or is a glioma. In an embodiment, the cancer treated is a metastatic melanoma.

This invention also provides a composition comprising a fusion protein as described herein. In an embodiment, the composition is a pharmaceutical composition. In an embodiment the composition or pharmaceutical composition comprising one or more of the fusion proteins described herein is substantially pure with regard to the fusion protein. A composition or pharmaceutical composition comprising one or more of the fusion proteins described herein is "substantially pure" with regard to the antibody or fragment when at least about 60 to 75% of a sample of the composition or pharmaceutical composition exhibits a single species of the fusion protein. A substantially pure composition or pharmaceutical composition comprising one or more of the fusion proteins described herein can comprise, in the portion thereof which is the fusion protein, 60%, 70%, 80% or 90% of the fusion protein of the single species, more usually about 95%, and preferably over 99%. Fusion protein purity or homogeneity may be tested by a number of means well known in the art, such as polyacrylamide gel electrophoresis or HPLC.

The invention also encompasses compositions comprising the described fusion proteins and a carrier. The carrier may comprise one or more pharmaceutically-acceptable carrier components. Such pharmaceutically-acceptable carrier components are widely known in the art.

In an embodiment, the subject being treated for cancer via a method herein is also treated with a chemotherapuetic agents, such as a cytotoxic agent. In an embodiment, the cytotoxic agent is doxorubicin. In an embodiment, the cytotoxic agent is a maytansinoid. In an embodiment, the cytotoxic agent an alkylating agent, an anti-metabolite, a plant alkaloid or terpenoid, or a cytotoxic antibiotic. In embodiments, the cytotoxic agent is cyclophosphamide, bleomycin, etoposide, platinum agent (cisplatin), fluorouracil, vincristine, methotrexate, taxol, epirubicin, leucovorin (folinic acid), or irinotecan.

Administration as used herein, unless otherwise stated, can be auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethral, and vaginal.

In an embodiment, the fusion protein of the invention is administered systemically in the methods described herein. In an embodiment, the fusion protein of the invention is administered locally in the methods described herein. In an embodiment, the fusion protein of the invention is administered directly to the tumor in the methods described herein, for example by injection or cannulation.

In an embodiment, the antibody or antibody fragment of the invention is administered systemically in the methods described herein. In an embodiment, the antibody or antibody fragment of the invention is administered locally in the methods described herein. In an embodiment, the antibody or antibody fragment of the invention is administered directly to the tumor in the methods described herein, for example by injection or cannulation.

In an embodiment, "determining" as used herein means experimentally determining.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

The existing technologies for T-cell based immunotherapies regarding B7/CD28 family members work by blockade of the B7/CD28 family members. In contrast, the expression patterns and functions of BTNL9 and ERMAP, two members of the butyrophilin family, are different from CTLA-4 and PD-1 and their ligands, therefore, the BTNL9 pathway and the ERMAP pathway regulate the immune system at the different times and locations.

Figure 1B:
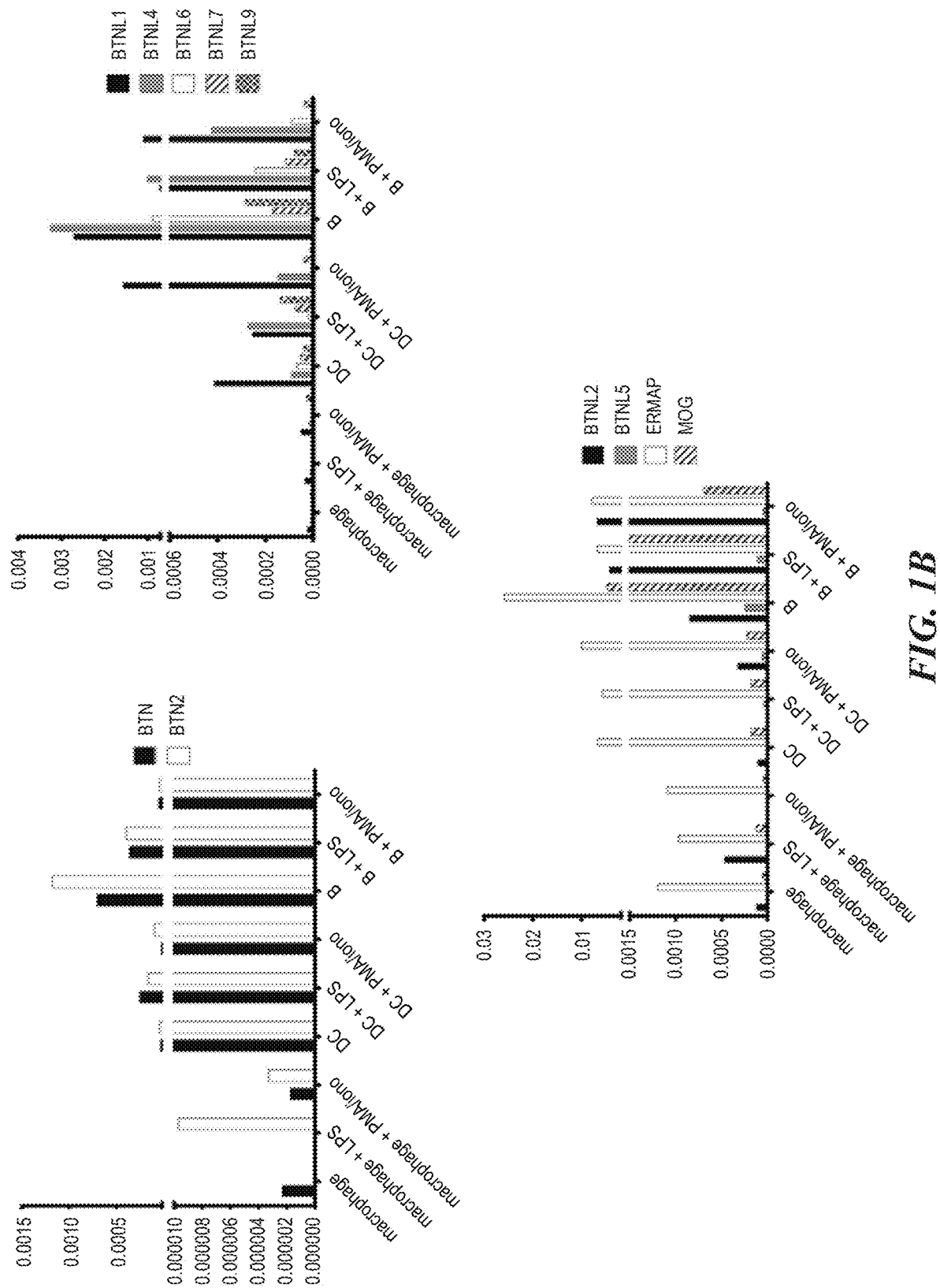

Example 1 mRNA expression of BTNL9, ERMAP and other members of the butyrophilin family in tissues and antigen-presenting cells: The butyrophilin family is related to the B7 family, but their expression and functions in the immune system are largely unknown. Using Real-Time RT-PCR, it was determined that BTNL9 and ERMAP, together with other family members, were widely expressed in many tissues and antigen-presenting cells (FIG. 1).

Example 2

Figure 2A:
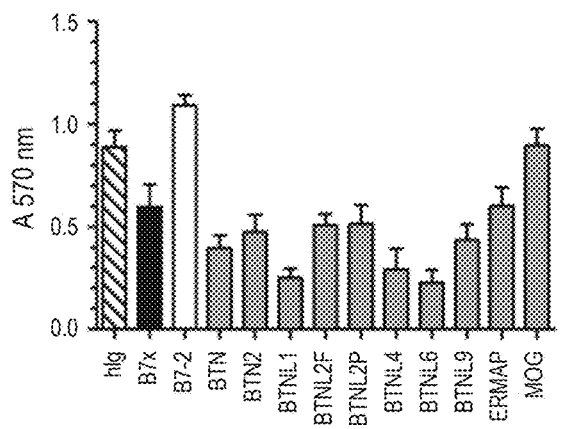
FIG. 2A-2C. Most recombinant BTN and BTNL family members inhibit the function of anti-CD3-activated primary mouse T cells. T cells were isolated from mouse spleen and lymph nodes by magnetic cell separation and activated with 2.5 µg/mL plate-bound anti-CD3 in the presence of 4 µg/mL plate-bound BTN- and BTNL-human Ig recombinant fusion proteins. (A) All BTN and BTNL fusion proteins, with the exception of ERMAP and MOG, reduce the metabolic activity of CD4+ T cells by 3 days post-activation. Human Ig (hIg), B7x-hIg, and B7.2-hIg fusion proteins are included as baseline, negative, and positive controls for activation, respectively. (B) BTN and BTNL fusion proteins reduce proliferation of activated CD4+ and CD8+ T cells. CD90.2+ T-cells were pulsed with CFSE prior to activation for 4 days, and stained with fluorescence-labeled antibodies to CD4 and CD8. CD4+ T cells (upper panel) showed reduced proliferation in the presence of BTN, BTN2, BTNL1, BTNL2 (full- and partial length), BTNL4, BTNL6, BTNL9, and ERMAP, and CD8+ T cells (panel) showed reduced proliferation in the presence of BTN, BTN2, BTNL1, BTNL2 (full- and partial-length), BTNL4, BTNL6, and BTNL9. The division indices, i.e., average number of divisions (closed bars), and percent divided (open bars) of CD4+ and CD8+ T cells are shown to the right of the histograms. (C) Secretion of the cytokines IFN-γ, IL-2, TNF-α, and IL-17A by CD4+ T cells 2 days post-activation is reduced in the presence of BTN and BTNL fusion proteins compared to baseline (hIg).
Figure 2B:
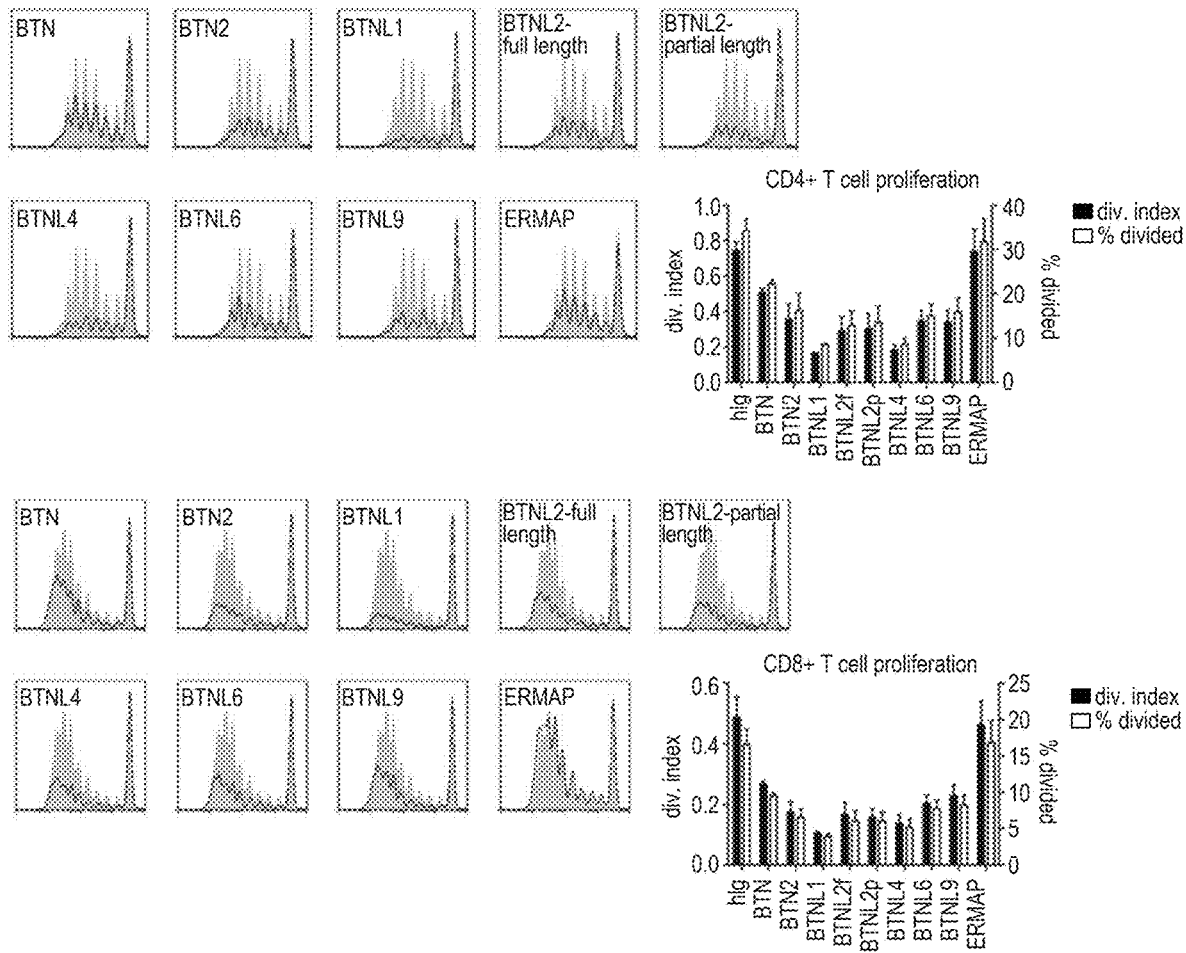
Figure 2C:
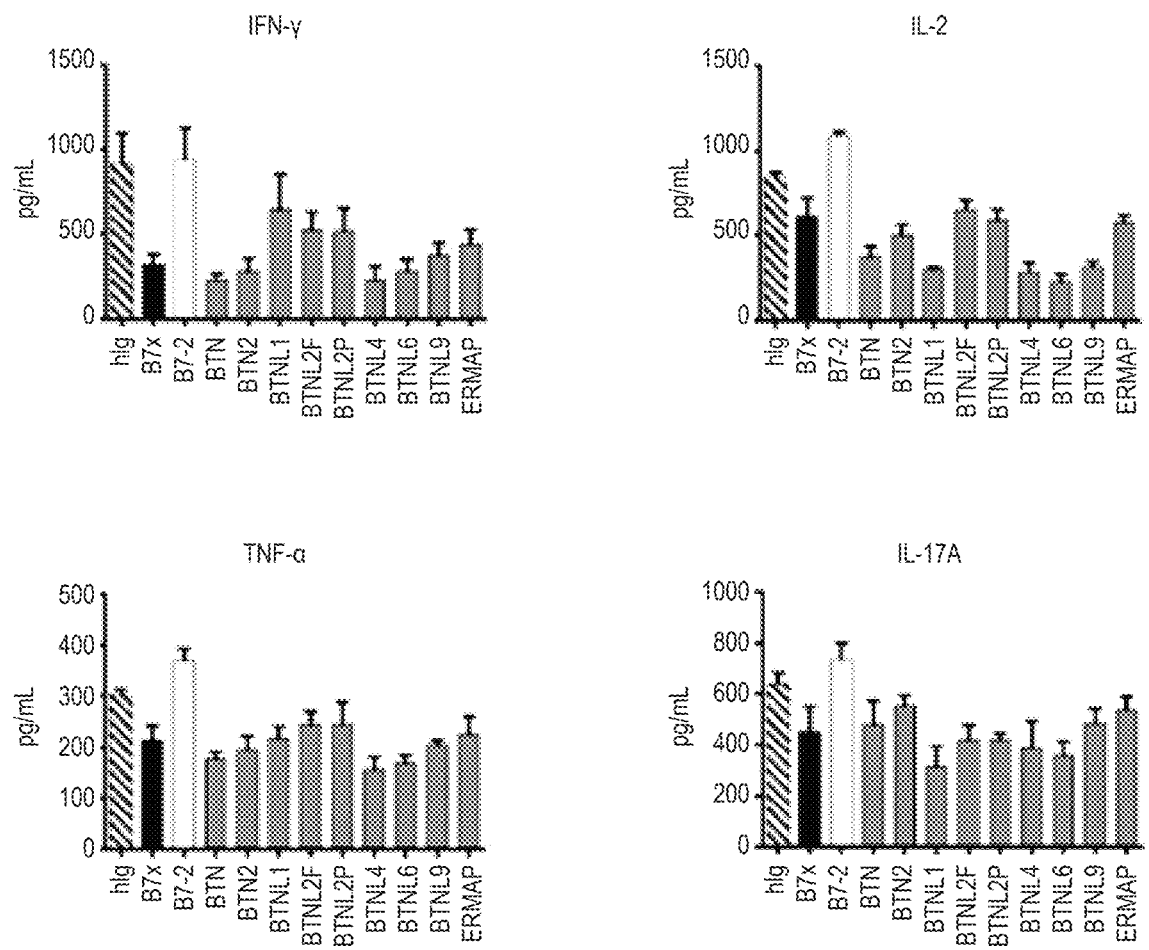

BTNL9, ERMAP and some other members of the butyrophilin family inhibit T cell function: It was examined whether BTNL9, ERMAP and other members of the butyrophilin family were able to regulate T-cell function using a system modified from previous studies (PNAS, 110: 9879-9884, 2013). In this system, purified T cells were activated with plate-bound mAb to CD3 and the activation of T cells was determined on days 3 and T cell-derived cytokines were determined on day 2. It was determined that BTNL9 inhibited both CD4 and CD8 T cell proliferation and cytokine production, while ERMAP inhibited CD4, but not CD8 T cell proliferation (FIG. 2).

Example 3

Figure 3A:
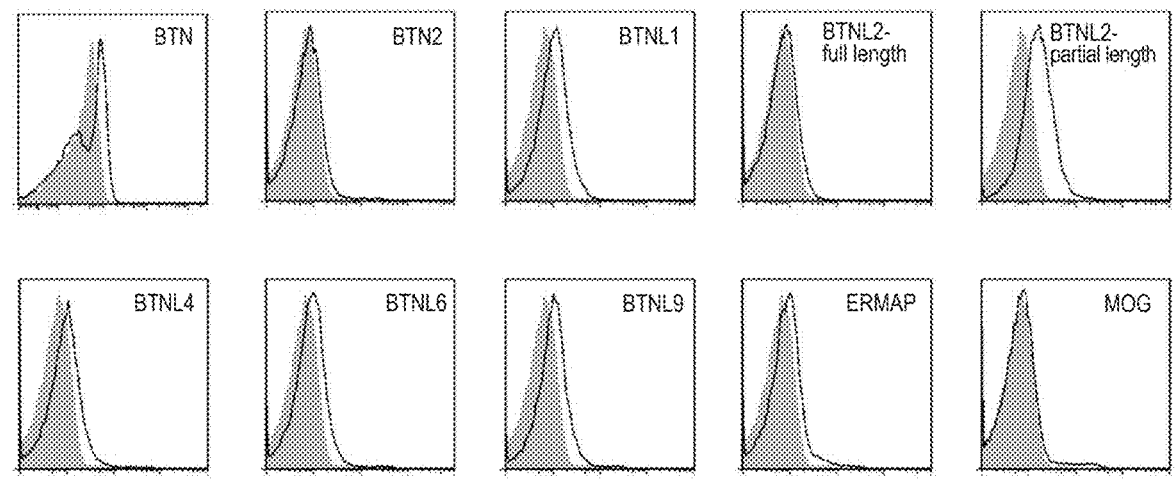
FIG. 3A-3B. CD4+ (A) and CD8+ (B) T cells activated for 3 days express a receptor for BTN and BTNL proteins. Total lymph node cells were activated by plate-bound 2.5 μg/mL anti-CD3 and incubated with biotinylated BTN-, BTNL-hIg, or hIg-fusion protein, stained with fluorescence-labeled antibodies to CD4 and CD8, and evaluated for fusion protein binding with fluorescence-labeled streptavidin. Both activated T cell subsets express a receptor for all BTN and BTNL family members, with the exception of MOG, which is consistent with functional data.
Figure 3B:
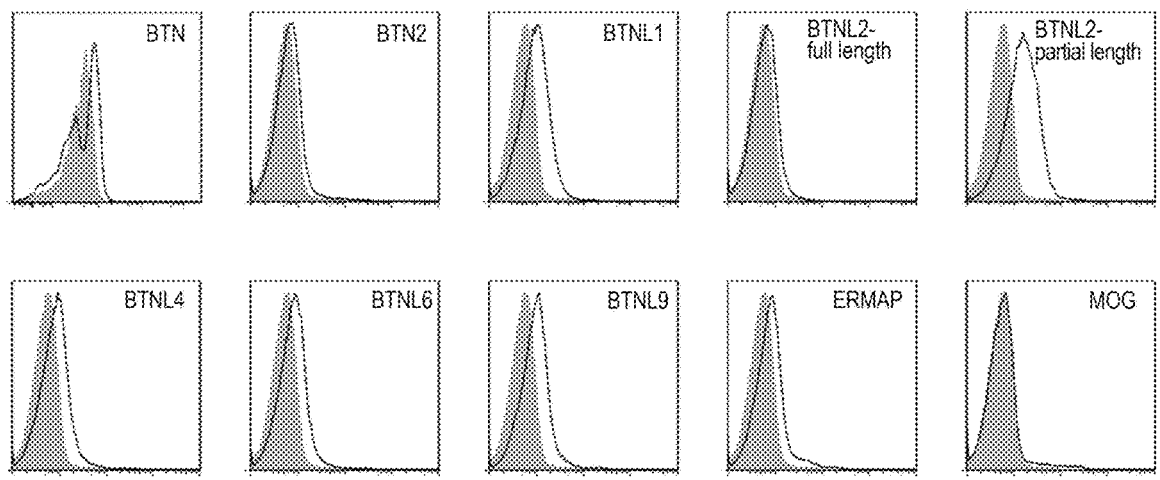

Activated T cells have receptors for BTNL9, ERMAP and some other members of the butyrophilin family: Because BTNL9 and ERMAP inhibited T cell function, it was examined if activated T cells express receptors for these molecules. It was determined that BTNL9-Ig, BTNL9, ERMAP-Ig and other Ig fusion proteins of some members of the butyrophilin family bound to activated CD4 and CD8 T cells which were activated for three days (FIG. 3).

Example 4

Figure 4:
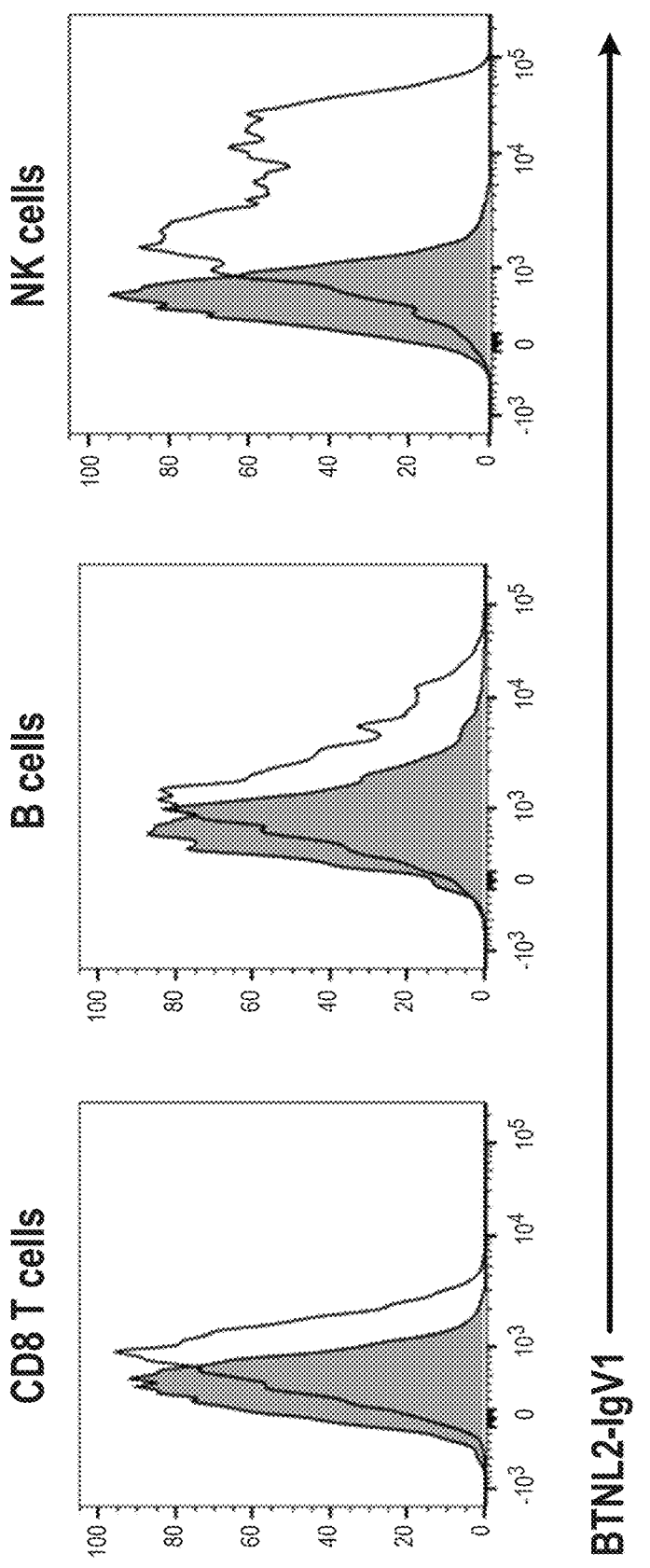
FIG. 4. The IgV1 domain of human BTNL2 bound human CD8 T cells, human B cells, and human NK cells. BTNL2-IgV1-Ig protein (open histograms) and control Ig (shaded histograms) are shown in FACS assays.

The IgV1 domain of Human BTNL2 is the functional domain. As shown in FIG. 4, the IgV1 domain of human BTNL2 bound human CD8 T cells, human B cells, and human NK cells. BTNL2-IgV1-Ig protein (open histograms) and control Ig (shaded histograms) are shown in FACS assays. Sequence shown is SEQ ID NO:5.

Example 5

Figure 5:
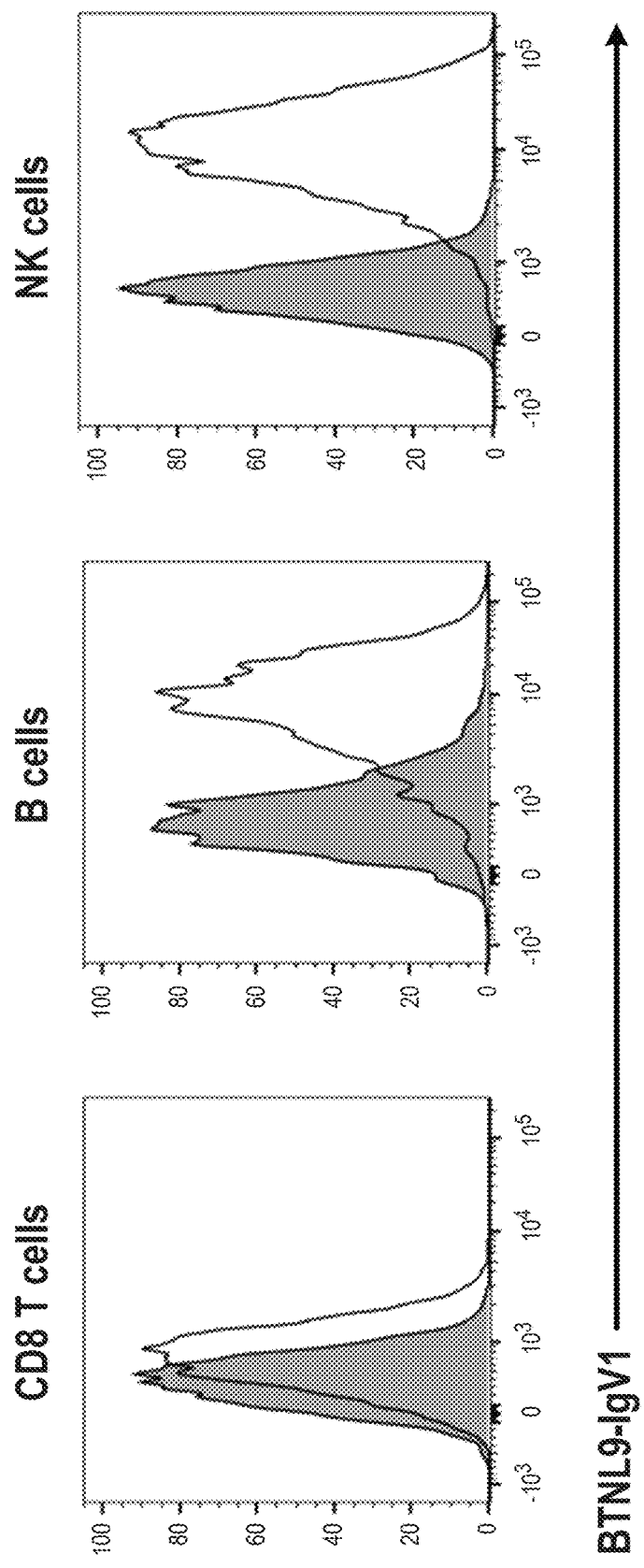
FIG. 5. The IgV1 domain of human BTNL9 bound human CD8 T cells, human B cells, and human NK cells. BTNL9-IgV1-Ig protein (open histograms) and control Ig (shaded histograms) are shown in FACS assays.

The IgV1 domain of Human BTNL9 is the functional domain. As shown in FIG. 5, the IgV1 domain of human BTNL9 bound human CD8 T cells, human B cells, and human NK cells. BTNL9-IgV1-Ig protein (open histograms) and control Ig (shaded histograms) are shown in FACS assays. Sequence shown is SEQ ID NO:6.

What is claimed is:

1. A method of treating a tumor in a subject, comprising administering to the subject a therapeutically effective amount of a polypeptide comprising an isolated plasma-soluble polypeptide comprising a soluble portion of short form BTNL2 having the amino acid sequence set forth in SEQ ID NO: 4 and excluding the amino acid sequence set forth in SEQ ID NO: 3, wherein the polypeptide treats the tumor.

2. The method of claim 1, wherein the tumor is a tumor of a breast, lung, thyroid, melanoma, pancreas, ovary, liver, bladder, colon, prostate, kidney, esophagus, or is a hematological tumor, or wherein the tumor is a lymphoid organ tumor.

3. The method of claim 1, wherein the isolated plasma-soluble polypeptide is a fusion protein.

4. The method of claim 3, wherein the fusion protein comprises an Fc portion of an immunoglobulin G.

5. A method of treating an autoimmune disease in a subject, comprising administering to the subject a therapeutically effective amount of an isolated plasma-soluble polypeptide comprising a soluble portion of short form BTNL2 having the amino acid sequence set forth in SEQ ID NO: 4 and excluding the amino acid sequence set forth in SEQ ID NO: 3, wherein the polypeptide treats the autoimmune disease in the subject.

6. The method of claim 5, wherein the plasma-soluble polypeptide is a fusion protein.

7. The method of claim 6, wherein the fusion protein comprises an Fc portion of immunoglobulin G.

8. The method of claim 7, wherein the Fc portion of immunoglobulin G is fused to the soluble portion of BTNL2.

9. An isolated chimeric nucleic acid encoding the polypeptide of claim 1.

10. An isolated chimeric nucleic acid comprising a first set of nucleotides which encode a soluble portion of short form BTNL2 having the amino acid sequence set forth in SEQ ID NO: 4 and excluding the amino acid sequence set forth in SEQ ID NO: 3.

11. The isolated chimeric nucleic acid of claim 10, further comprising a second set of nucleotides which encode an Fc portion of an immunoglobulin G.

12. The isolated chimeric nucleic acid of claim 11, wherein the Fc portion of immunoglobulin G lacks a C-terminal lysine.

13. The isolated chimeric nucleic acid of claim 12, wherein the second set of nucleotides is recombinantly engineered to encode the Fc portion of immunoglobulin G lacking a C-terminal lysine.

14. The isolated chimeric nucleic acid of claim 11, wherein the first set of nucleotides and the second set of nucleotides are disposed sequentially within the isolated chimeric nucleic acid.

15. The isolated chimeric nucleic acid of claim 14, wherein the first set of nucleotides and the second set of nucleotides encode a fusion protein.

* * * * *

SEQUENCE LISTING

```
<160> NUMBER OF SEQ ID NOS: 8

<210> SEQ ID NO 1
<211> LENGTH: 535
<212> TYPE: PRT
<213> ORGANISM: Homo sapiens

<400> SEQUENCE: 1

Met Val Asp Leu Ser Val Ser Pro Asp Ser Leu Lys Pro Val Ser Leu
1               5                   10                  15

Thr Ser Ser Leu Val Phe Leu Met His Leu Leu Leu Leu Gln Pro Gly
            20                  25                  30

Glu Pro Ser Ser Glu Val Lys Val Leu Gly Pro Glu Tyr Pro Ile Leu
        35                  40                  45

Ala Leu Val Gly Glu Glu Val Glu Phe Pro Cys His Leu Trp Pro Gln
    50                  55                  60

Leu Asp Ala Gln Gln Met Glu Ile Arg Trp Phe Arg Ser Gln Thr Phe
65                  70                  75                  80

Asn Val Val His Leu Tyr Gln Glu Gln Gln Glu Leu Pro Gly Arg Gln
                85                  90                  95

Met Pro Ala Phe Arg Asn Arg Thr Lys Leu Val Lys Asp Asp Ile Ala
            100                 105                 110

Tyr Gly Ser Val Val Leu Gln Leu His Ser Ile Ile Pro Ser Asp Lys
        115                 120                 125

Gly Thr Tyr Gly Cys Arg Phe His Ser Asp Asn Phe Ser Gly Glu Ala
    130                 135                 140

Leu Trp Glu Leu Glu Val Ala Gly Leu Gly Ser Asp Pro His Leu Ser
145                 150                 155                 160

Leu Glu Gly Phe Lys Glu Gly Gly Ile Gln Leu Arg Leu Arg Ser Ser
                165                 170                 175

Gly Trp Tyr Pro Lys Pro Lys Val Gln Trp Arg Asp His Gln Gly Gln
            180                 185                 190

Cys Leu Pro Pro Glu Phe Glu Ala Ile Val Trp Asp Ala Gln Asp Leu
        195                 200                 205

Phe Ser Leu Glu Thr Ser Val Val Arg Ala Gly Ala Leu Ser Asn
    210                 215                 220

Val Ser Val Ser Ile Gln Asn Leu Leu Leu Ser Gln Lys Lys Glu Leu
225                 230                 235                 240

Val Val Gln Ile Ala Asp Val Phe Val Pro Gly Ala Ser Ala Trp Lys
                245                 250                 255

Ser Ala Phe Val Ala Thr Leu Pro Leu Leu Val Leu Ala Ala Leu
            260                 265                 270

Ala Leu Gly Val Leu Arg Lys Gln Arg Arg Ser Arg Glu Lys Leu Arg
        275                 280                 285

Lys Gln Ala Glu Lys Arg Gln Glu Lys Leu Thr Ala Glu Leu Glu Lys
```

```
            290                 295                 300
Leu Gln Thr Glu Leu Asp Trp Arg Arg Ala Glu Gly Gln Ala Glu Trp
305                 310                 315                 320

Arg Ala Ala Gln Lys Tyr Ala Val Asp Val Thr Leu Asp Pro Ala Ser
                325                 330                 335

Ala His Pro Ser Leu Glu Val Ser Glu Asp Gly Lys Ser Val Ser Ser
                340                 345                 350

Arg Gly Ala Pro Pro Gly Pro Ala Pro Gly His Pro Gln Arg Phe Ser
            355                 360                 365

Glu Gln Thr Cys Ala Leu Ser Leu Glu Arg Phe Ser Ala Gly Arg His
        370                 375                 380

Tyr Trp Glu Val His Val Gly Arg Arg Ser Arg Trp Phe Leu Gly Ala
385                 390                 395                 400

Cys Leu Ala Ala Val Pro Arg Ala Gly Pro Ala Arg Leu Ser Pro Ala
                405                 410                 415

Ala Gly Tyr Trp Val Leu Gly Leu Trp Asn Gly Cys Glu Tyr Phe Val
            420                 425                 430

Leu Ala Pro His Arg Val Ala Leu Thr Leu Arg Val Pro Pro Arg Arg
        435                 440                 445

Leu Gly Val Phe Leu Asp Tyr Glu Ala Gly Glu Leu Ser Phe Phe Asn
    450                 455                 460

Val Ser Asp Gly Ser His Ile Phe Thr Phe His Asp Thr Phe Ser Gly
465                 470                 475                 480

Ala Leu Cys Ala Tyr Phe Arg Pro Arg Ala His Asp Gly Gly Glu His
                485                 490                 495

Pro Asp Pro Leu Thr Ile Cys Pro Leu Pro Val Arg Gly Thr Gly Val
            500                 505                 510

Pro Glu Glu Asn Asp Ser Asp Thr Trp Leu Gln Pro Tyr Glu Pro Ala
        515                 520                 525

Asp Pro Ala Leu Asp Trp Trp
    530                 535

<210> SEQ ID NO 2
<211> LENGTH: 475
<212> TYPE: PRT
<213> ORGANISM: Homo sapiens

<400> SEQUENCE: 2

Met Glu Met Ala Ser Ser Ala Gly Ser Trp Leu Ser Gly Cys Leu Ile
1               5                   10                  15

Pro Leu Val Phe Leu Arg Leu Ser Val His Val Ser Gly His Ala Gly
                20                  25                  30

Asp Ala Gly Lys Phe His Val Ala Leu Leu Gly Gly Thr Ala Glu Leu
            35                  40                  45

Leu Cys Pro Leu Ser Leu Trp Pro Gly Thr Val Pro Lys Glu Val Arg
        50                  55                  60

Trp Leu Arg Ser Pro Phe Pro Gln Arg Ser Gln Ala Val His Ile Phe
65                  70                  75                  80

Arg Asp Gly Lys Asp Gln Asp Glu Asp Leu Met Pro Glu Tyr Lys Gly
                85                  90                  95

Arg Thr Val Leu Val Arg Asp Ala Gln Glu Gly Ser Val Thr Leu Gln
            100                 105                 110

Ile Leu Asp Val Arg Leu Glu Asp Gln Gly Ser Tyr Arg Cys Leu Ile
        115                 120                 125
```

```
Gln Val Gly Asn Leu Ser Lys Glu Asp Thr Val Ile Leu Gln Val Ala
130                 135                 140

Ala Pro Ser Val Gly Ser Leu Ser Pro Ser Ala Val Ala Leu Ala Val
145                 150                 155                 160

Ile Leu Pro Val Leu Val Leu Ile Met Val Cys Leu Cys Leu Ile
                165                 170                 175

Trp Lys Gln Arg Arg Ala Lys Glu Lys Leu Leu Tyr Glu His Val Thr
                180                 185                 190

Glu Val Asp Asn Leu Leu Ser Asp His Ala Lys Glu Lys Gly Lys Leu
                195                 200                 205

His Lys Ala Val Lys Lys Leu Arg Ser Glu Leu Lys Leu Lys Arg Ala
210                 215                 220

Ala Ala Asn Ser Gly Trp Arg Arg Ala Arg Leu His Phe Val Ala Val
225                 230                 235                 240

Thr Leu Asp Pro Asp Thr Ala His Pro Lys Leu Ile Leu Ser Glu Asp
                245                 250                 255

Gln Arg Cys Val Arg Leu Gly Asp Arg Arg Gln Pro Val Pro Asp Asn
                260                 265                 270

Pro Gln Arg Phe Asp Phe Val Val Ser Ile Leu Gly Ser Glu Tyr Phe
                275                 280                 285

Thr Thr Gly Cys His Tyr Trp Glu Val Tyr Val Gly Asp Lys Thr Lys
                290                 295                 300

Trp Ile Leu Gly Val Cys Ser Glu Ser Val Ser Arg Lys Gly Lys Val
305                 310                 315                 320

Thr Ala Ser Pro Ala Asn Gly His Trp Leu Leu Arg Gln Ser Arg Gly
                325                 330                 335

Asn Glu Tyr Glu Ala Leu Thr Ser Pro Gln Thr Ser Phe Arg Leu Lys
                340                 345                 350

Glu Pro Pro Arg Cys Val Gly Ile Phe Leu Asp Tyr Glu Ala Gly Val
                355                 360                 365

Ile Ser Phe Tyr Asn Val Thr Asn Lys Ser His Ile Phe Thr Phe Thr
                370                 375                 380

His Asn Phe Ser Gly Pro Leu Arg Pro Phe Phe Glu Pro Cys Leu His
385                 390                 395                 400

Asp Gly Gly Lys Asn Thr Ala Pro Leu Val Ile Cys Ser Glu Leu His
                405                 410                 415

Lys Ser Glu Glu Ser Ile Val Pro Arg Pro Glu Gly Lys Gly His Ala
                420                 425                 430

Asn Gly Asp Val Ser Leu Lys Val Asn Ser Ser Leu Leu Pro Pro Lys
                435                 440                 445

Ala Pro Glu Leu Lys Asp Ile Ile Leu Ser Leu Pro Pro Asp Leu Gly
450                 455                 460

Pro Ala Leu Gln Glu Leu Lys Ala Pro Ser Phe
465                 470                 475

<210> SEQ ID NO 3
<211> LENGTH: 456
<212> TYPE: PRT
<213> ORGANISM: Homo sapiens

<400> SEQUENCE: 3

Met Val Asp Cys Pro Arg Tyr Ser Leu Ser Gly Val Ala Ala Ser Phe
1               5                   10                  15

Leu Phe Val Leu Leu Thr Ile Lys His Pro Asp Asp Phe Arg Val Val
                20                  25                  30
```

-continued

Gly Pro Asn Leu Pro Ile Leu Ala Lys Val Gly Glu Asp Ala Leu Leu
            35                  40                  45

Thr Cys Gln Leu Leu Pro Lys Arg Thr Thr Ala His Met Glu Val Arg
    50                  55                  60

Trp Tyr Arg Ser Asp Pro Ala Met Pro Val Ile Met Tyr Arg Asp Gly
65                  70                  75                  80

Ala Val Val Thr Gly Leu Pro Met Glu Gly Tyr Gly Arg Ala Glu
                85                  90                  95

Trp Met Glu Asp Ser Thr Glu Glu Gly Ser Val Ala Leu Lys Ile Arg
            100                 105                 110

Gln Val Gln Pro Ser Asp Asp Gly Gln Tyr Trp Cys Arg Phe Gln Glu
            115                 120                 125

Gly Asp Tyr Trp Arg Glu Thr Ser Val Leu Leu Gln Val Ala Ala Leu
        130                 135                 140

Gly Ser Ser Pro Asn Ile His Val Glu Gly Leu Gly Glu Gly Glu Val
145                 150                 155                 160

Gln Leu Val Cys Thr Ser Arg Gly Trp Phe Pro Glu Pro Glu Val His
                165                 170                 175

Trp Glu Gly Ile Trp Gly Glu Lys Leu Met Ser Phe Ser Glu Asn His
            180                 185                 190

Val Pro Gly Glu Asp Gly Leu Phe Tyr Val Glu Asp Thr Leu Met Val
            195                 200                 205

Arg Asn Asp Ser Val Glu Thr Ile Ser Cys Phe Ile Tyr Ser His Gly
210                 215                 220

Leu Arg Glu Thr Gln Glu Ala Thr Ile Ala Leu Ser Glu Arg Leu Gln
225                 230                 235                 240

Thr Glu Leu Val Ser Val Ser Val Ile Gly His Ser Gln Pro Ser Pro
                245                 250                 255

Val Gln Val Gly Glu Asn Ile Glu Leu Thr Cys His Leu Ser Pro Gln
            260                 265                 270

Thr Asp Ala Gln Asn Leu Glu Val Arg Trp Leu Arg Ser Arg Tyr Tyr
        275                 280                 285

Pro Ala Val His Val Tyr Ala Asn Gly Thr His Val Ala Gly Glu Gln
        290                 295                 300

Met Val Glu Tyr Lys Gly Arg Thr Ser Leu Val Thr Asp Ala Ile His
305                 310                 315                 320

Glu Gly Lys Leu Thr Leu Gln Ile His Asn Ala Arg Thr Ser Asp Glu
                325                 330                 335

Gly Gln Tyr Arg Cys Leu Phe Gly Lys Asp Gly Val Tyr Gln Glu Ala
            340                 345                 350

Arg Val Asp Val Gln Val Thr Ala Val Gly Ser Thr Pro Arg Ile Thr
        355                 360                 365

Arg Glu Val Leu Lys Asp Gly Met Gln Leu Arg Cys Thr Ser Asp
370                 375                 380

Gly Trp Phe Pro Arg Pro His Val Gln Trp Arg Asp Arg Asp Gly Lys
385                 390                 395                 400

Thr Met Pro Ser Phe Ser Glu Ala Phe Gln Gln Gly Ser Gln Glu Leu
                405                 410                 415

Phe Gln Val Glu Thr Leu Leu Val Thr Asn Gly Ser Met Val Asn
            420                 425                 430

Val Thr Cys Ser Ile Ser Leu Pro Leu Gly Gln Glu Lys Thr Ala Arg
        435                 440                 445

```
Phe Pro Leu Ser Asp Ser Lys Ile
    450                 455
```

<210> SEQ ID NO 4
<211> LENGTH: 260
<212> TYPE: PRT
<213> ORGANISM: Homo sapiens

<400> SEQUENCE: 4

```
Met Val Asp Cys Pro Arg Tyr Ser Leu Ser Gly Val Ala Ala Ser Phe
1               5                   10                  15

Leu Phe Val Leu Leu Thr Ile Lys His Pro Asp Asp Phe Arg Val Val
            20                  25                  30

Gly Pro Asn Leu Pro Ile Leu Ala Lys Val Gly Glu Asp Ala Leu Leu
                35                  40                  45

Thr Cys Gln Leu Leu Pro Lys Arg Thr Thr Ala His Met Glu Val Arg
    50                  55                  60

Trp Tyr Arg Ser Asp Pro Ala Met Pro Val Ile Met Tyr Arg Asp Gly
65                  70                  75                  80

Ala Val Val Thr Gly Leu Pro Met Glu Gly Tyr Gly Gly Arg Ala Glu
                85                  90                  95

Trp Met Glu Asp Ser Thr Glu Glu Gly Ser Val Ala Leu Lys Ile Arg
            100                 105                 110

Gln Val Gln Pro Ser Asp Asp Gly Gln Tyr Trp Cys Arg Phe Gln Glu
        115                 120                 125

Gly Asp Tyr Trp Arg Glu Thr Ser Val Leu Leu Gln Val Ala Ala Leu
    130                 135                 140

Gly Ser Ser Pro Asn Ile His Val Glu Gly Leu Gly Glu Gly Glu Val
145                 150                 155                 160

Gln Leu Val Cys Thr Ser Arg Gly Trp Phe Pro Glu Pro Glu Val His
                165                 170                 175

Trp Glu Gly Ile Trp Gly Glu Lys Leu Met Ser Phe Ser Glu Asn His
            180                 185                 190

Val Pro Gly Glu Asp Gly Leu Phe Tyr Val Glu Asp Thr Leu Met Val
        195                 200                 205

Arg Asn Asp Ser Val Glu Thr Ile Ser Cys Phe Ile Tyr Ser His Gly
    210                 215                 220

Leu Arg Glu Thr Gln Glu Ala Thr Ile Ala Leu Ser Glu Arg Leu Gln
225                 230                 235                 240

Thr Glu Leu Val Ser Val Ser Val Ile Gly His Ser Gln Pro Ser Pro
                245                 250                 255

Val Gln Val Gly
        260
```

<210> SEQ ID NO 5
<211> LENGTH: 129
<212> TYPE: PRT
<213> ORGANISM: Homo sapiens

<400> SEQUENCE: 5

```
Lys Gln Ser Glu Asp Phe Arg Val Ile Gly Pro Ala His Pro Ile Leu
1               5                   10                  15

Ala Gly Val Gly Glu Asp Ala Leu Leu Thr Cys Gln Leu Leu Pro Lys
            20                  25                  30

Arg Thr Thr Met His Val Glu Val Arg Trp Tyr Arg Ser Glu Pro Ser
                35                  40                  45
```

```
Thr Pro Val Phe Val His Arg Asp Gly Val Glu Val Thr Glu Met Gln
    50              55                  60

Met Glu Glu Tyr Arg Gly Trp Val Glu Trp Ile Glu Asn Gly Ile Ala
 65              70                  75                  80

Lys Gly Asn Val Ala Leu Lys Ile His Asn Ile Gln Pro Ser Asp Asn
                 85                  90                  95

Gly Gln Tyr Trp Cys His Phe Gln Asp Gly Asn Tyr Cys Gly Glu Thr
            100                 105                 110

Ser Leu Leu Leu Lys Val Ala Gly Leu Gly Ser Ala Pro Ser Ile His
            115                 120                 125

Met

<210> SEQ ID NO 6
<211> LENGTH: 124
<212> TYPE: PRT
<213> ORGANISM: Homo sapiens

<400> SEQUENCE: 6

Glu Val Lys Val Leu Gly Pro Glu Tyr Pro Ile Leu Ala Leu Val Gly
 1               5                  10                  15

Glu Glu Val Glu Phe Pro Cys His Leu Trp Pro Gln Leu Asp Ala Gln
                 20                  25                  30

Gln Met Glu Ile Arg Trp Phe Arg Ser Gln Thr Phe Asn Val Val His
             35                  40                  45

Leu Tyr Gln Glu Gln Gln Glu Leu Pro Gly Arg Gln Met Pro Ala Phe
 50                  55                  60

Arg Asn Arg Thr Lys Leu Val Lys Asp Asp Ile Ala Tyr Gly Ser Val
 65                  70                  75                  80

Val Leu Gln Leu His Ser Ile Ile Pro Ser Lys Gly Thr Tyr Gly
                 85                  90                  95

Cys Arg Phe His Ser Asp Asn Phe Ser Gly Glu Ala Leu Trp Glu Leu
                100                 105                 110

Glu Val Ala Gly Leu Gly Ser Asp Pro His Leu Ser
            115                 120

<210> SEQ ID NO 7
<211> LENGTH: 5
<212> TYPE: PRT
<213> ORGANISM: Artificial Sequence
<220> FEATURE:
<223> OTHER INFORMATION: artificial linker sequence
<220> FEATURE:
<221> NAME/KEY: MISC_FEATURE
<222> LOCATION: (1)..(5)
<223> OTHER INFORMATION: sequence can be single or repeat 2, 3, 4, or 5
      times

<400> SEQUENCE: 7

Gly Gly Gly Gly Ser
 1               5

<210> SEQ ID NO 8
<211> LENGTH: 5
<212> TYPE: PRT
<213> ORGANISM: Artificial Sequence
<220> FEATURE:
<223> OTHER INFORMATION: artificial linker sequence
<220> FEATURE:
<221> NAME/KEY: MISC_FEATURE
<222> LOCATION: (1)..(5)
<223> OTHER INFORMATION: sequence can be single or repeat 2, 3, 4, or 5
      times
```

```
<400> SEQUENCE: 8

Glu Ala Ala Ala Lys
1               5
```